United States Patent [19]

Rydell

[11] Patent Number: 5,891,141
[45] Date of Patent: Apr. 6, 1999

[54] BIPOLAR ELECTROSURGICAL INSTRUMENT FOR CUTTING AND SEALING TUBULAR TISSUE STRUCTURES

[75] Inventor: Mark A. Rydell, Golden Valley, Minn.

[73] Assignee: Everest Medical Corporation, Minneapolis, Minn.

[21] Appl. No.: 65,242

[22] Filed: Apr. 23, 1998

Related U.S. Application Data

[63] Continuation-in-part of Ser. No. 922,052, Sep. 2, 1997, abandoned.

[51] Int. Cl.$^6$ .............................. A61B 17/36; A61B 17/32
[52] U.S. Cl. ................................ 606/45; 606/51; 606/167
[58] Field of Search .......................... 606/32, 34, 37–42, 606/45–52, 151, 157, 167, 205–211

[56] References Cited

U.S. PATENT DOCUMENTS 2,068,721   1/1937   Wappler et al. .
4,418,692  12/1983   Guay .
4,985,030   1/1991   Melzer et al. .
5,190,541   3/1993   Abele et al. .
5,269,780  12/1993   Roos .

*Primary Examiner*—Glenn K. Dawson
*Attorney, Agent, or Firm*—Nikolai, Mersereau & Dietz, P.A.

[57] ABSTRACT

An electrosurgical instrument for cutting and coagulating tubular tissue structures, especially tubular ones, includes a pair of spaced-apart electrodes that are stationarily mounted at the distal end of an elongated tubular barrel. A hook-shaped cutting member has an incline segment thereon for cooperating with a ramp formed at the distal end of the instrument. A tubular body structure to be severed is first brought into contact with electrodes and subjected to a RF current sufficient to coagulate and seal the same. Actuation of a lever on the instrument's handle causes the hook-shaped cutting member to deflect into a space containing the tissue structure and with continued actuation in a proximal direction causing a cutting edge on the hook of the cutting member to pass through and sever the tissue structure.

19 Claims, 7 Drawing Sheets

BIPOLAR ELECTROSURGICAL INSTRUMENT FOR CUTTING AND SEALING TUBULAR TISSUE STRUCTURES

CROSS REFERENCE TO RELATED INVENTION

This application is a Continuation-in-Part application of application Ser. No. 08/922,052, filed Sep. 2, 1997, entitled "BIPOLAR ELECTROSURGICAL INSTRUMENT FOR CUTTING AND SEALING TUBULAR TISSUE STRUCTURES", now abandoned.

BACKGROUND OF THE INVENTION

I. Field of the Invention

This invention relates generally to electrosurgical instruments for cutting and coagulating tissue, and more particularly to an instrument especially designed for cutting and sealing tubular body tissues, such as veins, fallopian tubes, vas deferens and the like.

II. Discussion of the Prior Art

In coronary bypass surgery, the bypass graft frequently comprises a segment of the great saphenous vein harvested from the patient's leg. In doing so, a surgeon would typically use a scalpel to cut longitudinally along the leg to expose the saphenous vein and then use blunt dissection techniques to remove a segment thereof which necessitates severing and subsequent coagulation of side branches emanating from the great saphenous vein to effect hemostasis before the original incision is closed. This procedure necessarily creates an extensive wound in the leg that often proves painful and slow to heal.

Less invasive techniques for harvesting the great saphenous vein have been devised and can be divided into either skin bridging or endoscopic. Skin bridging encompasses a procedure that involves making multiple incisions, ranging in length from 2 to 8 cms with retraction of the remaining overlying skin for access to the saphenous vein. Retraction is accomplished with a conventional blade-type retractor. The endoscopic technique offers an advantage of using only one or two incisions from 1 to 2 cms in length with the dissection then carried out with the assistance of an endoscope and specially designed endoscopic instruments that range in length from 24 to 45 cms. With the endoscopic technique, an instrument is used to create a tunnel around the great saphenous vein by entering a first of the transverse incisions and manipulating the instrument until its distal end is approximately midway to the adjacent incision, at which point the instrument is removed and reinserted in that adjacent incision and advanced towards the first incision until the tunnels meet. The process is then repeated along the length of the patient's leg.

While that instrument is useful in freeing the saphenous vein from adjacent connective tissue, a need exists for a companion instrument that can be used to cut and coagulate side branches emanating from the great saphenous vein. A cutting/coagulating forceps, such as that described in my earlier Rydell et al. U.S. Pat. No. 5,445,638, while readily adaptable to use in severing and sealing such branch veins is unnecessarily complex in that it requires a mechanism for manipulating the forceps jaws to make them open and close about the branch veins as well as a mechanism for actuating the cutting blade. Moreover, the scissors-style handle used on my earlier instrument is not ergonomically well suited to cutting and sealing side branches encountered when harvesting a segment of the saphenous vein for use in bypass surgery.

SUMMARY OF THE INVENTION

The present invention obviates the aforementioned drawbacks of my earlier design in that it does not require pivotally movable forceps jaws nor a mechanism for actuating same. In accordance with a first embodiment of the present invention, there is provided an electrosurgical instrument especially designed for cutting and coagulating tubular tissue structures that comprises an elongated tubular barrel having an in-line handle at a proximal end thereof and a pair of resilient metal wire electrodes, each having a pair of legs joined at one end thereof to form a generally U-shape at its distal end. The electrodes are supported in an insulating support member that is affixed to the distal end of the barrel and maintains the electrodes in parallel, spaced-apart, cantilevered relation with a predetermined gap therebetween. The support member includes first and second pairs of longitudinally extending bores, at least one of each pair communicating with the lumen of the barrel for receiving the legs of the pair of electrodes therein. The electrode support member further includes a longitudinal slot that extends transverse to planes in which the legs of the pair of electrodes reside. The slot is midway between the pairs of legs of the electrodes. A hook-shaped cutting member is disposed in the slot and is longitudinally movable therein. One of the hook-shaped cutting members or the slot in the electrode support member includes a ramp surface. Disposed on the handle is an actuator that is coupled to the hook-shaped cutting member for imparting reciprocal longitudinal translation thereto. Conductors extend through the handle, the lumen of the barrel and the at least one of each pair of bores and is adapted to connect the pair of electrodes to a voltage source.

The gap between the first and second U-shaped wire electrodes is designed to be less than the thickness of the tubular tissue structures to be cut and coagulated, such that the pair of electrodes grip tubular tissue structures upon their being inserted between the pair of electrodes.

The hook-shaped cutting member is movable from a first position where the hook-shaped cutting member resides out of the gap to a second position disposed in the gap and abutting the electrode support member upon actuation of the handle actuator. The hook-shaped cutting member includes a sharpened concave portion which cuts through the tubular tissue structure as the cutting member is drawn in the proximal direction. The downward movement of the hook-shaped blade into the gap between the electrodes takes place by virtue of the engagement of the ramp which may be on either the hook-shaped cutting member or in the slot of the electrode support member, with a mating surface of the other during the actuation of the cutting member.

In an alternative embodiment, the electrodes comprise first and second wire segments and the hook-shaped cutting member is again designed to descend into the space between the two electrodes upon displacement of the cutting member in the proximal direction.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views refer to corresponding parts.

DESCRIPTION OF THE PREFERRED EMBODIMENT

Figure 1:
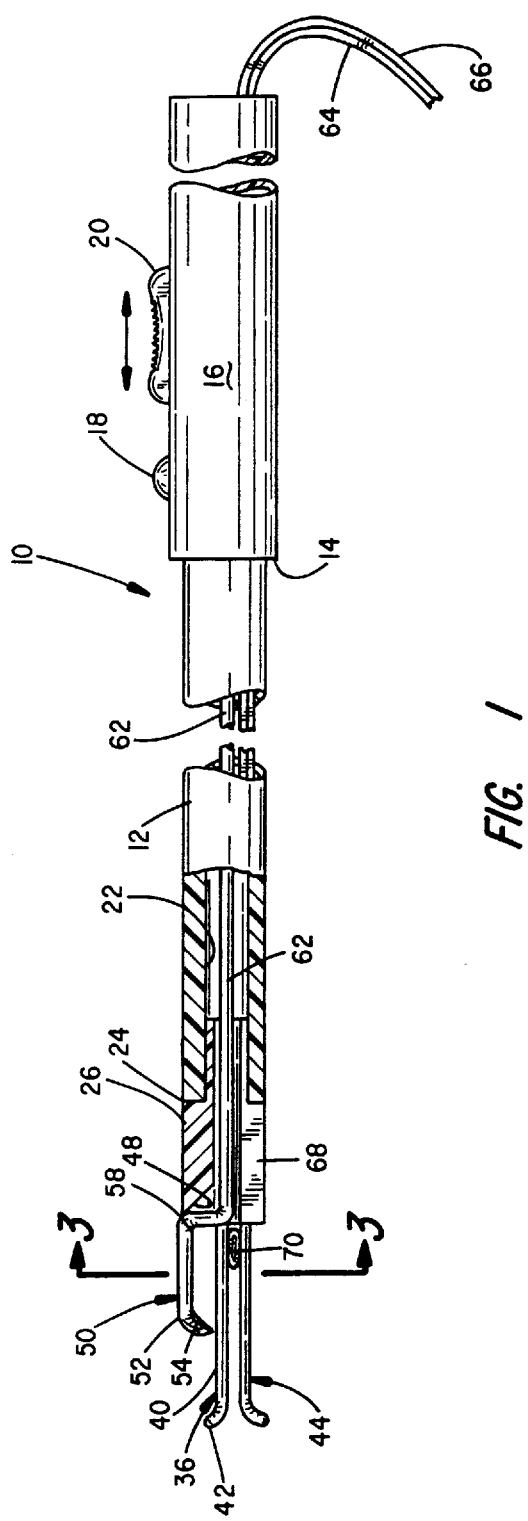
FIG. 1 is a partially sectioned side elevational view of the electrosurgical instrument comprising a preferred embodiment of the present invention.
Figure 2:
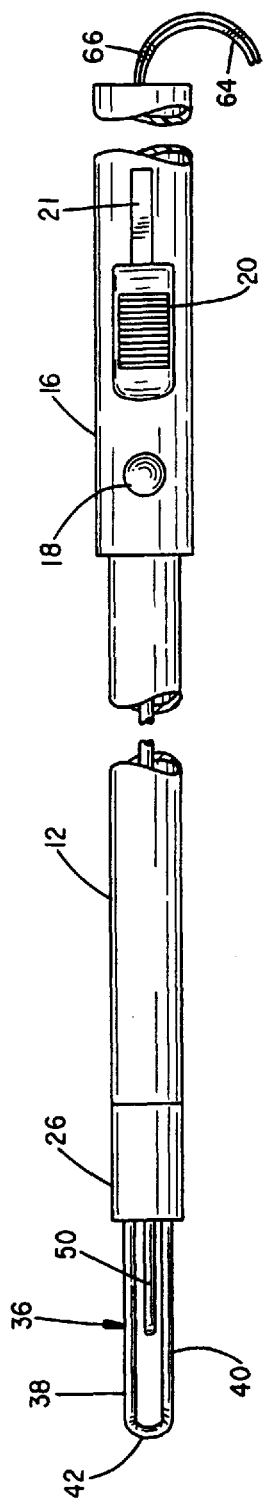
FIG. 2 is a top plan view of the instrument of FIG. 1.

As used in this specification, the term "proximal direction" refers to the right side of the drawing and "distal direction" refers to the left side of the drawing in FIGS. 1 and 2.

The electrosurgical instrument is referred to generally by numeral 10 and is seen to include an elongated tubular barrel 12 which may typically be about 12 in. in length and may have an outer diameter of about 0.2 in. Affixed to the proximal end 14 of the tubular barrel 12 is a handle member 16 on which is located an electrical push-button switch 18 and a thumb slide or lever 20. The tubular barrel has a lumen 22 and inserted into the lumen near the distal end 24 thereof is an electrode support member 26. The electrode support member is preferably formed from a suitable insulating material, such as ceramic or a high temperature plastic, and formed longitudinally inward from the face thereof are a plurality of bores 28, 30, 32 and 34. At least one of the bores 28 or 30 and one of the bores 32 or 34 extends through the entire length of the electrode support member 26 to allow an electrical connection to be made to the electrodes, as will be further explained.

Fitted into the bores 28 and 30 at the distal end of the electrode support member 26 is a first conductive resilient wire electrode 36 having first and second parallel, spaced-apart legs 38 and 40 that are integrally joined together at their distal ends by a slightly upturned transverse end portion 42. The proximal end of the legs 38 and 40 are dimensioned to fit into the bores 28 and 30, respectively. Likewise, the opposed parallel legs of a similar U-shaped electrode 44 are fitted into the bores 32 and 34 of the electrode support member 26. In this fashion, the U-shaped electrodes 36 and 44 are supported in a cantilevered fashion from the distal end of the electrode support member 26 and with a predetermined gap between the electrodes. The electrodes are preferably stainless steel wire that is bent to form the described U-shape configuration. They project about 0.375 in. from the distal end of the support 26 and the gap may be about 0.020 in.

Figure 3:
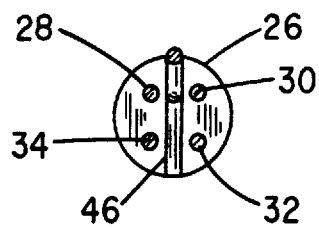
FIG. 3 is a cross-sectional view taken along the line 3—3 in FIG. 1.

The electrode support member 26 further includes a slot 46 (FIG. 3) that extends transverse to the planes defined by the parallel legs as at 38, 40 of electrode 36 and the corresponding parallel legs of the electrode 44 and is approximately midway between the bores in which the electrodes are supported. Formed internally of the slot 46 is a ramp surface 48 (FIG. 1).

The instrument 10 further includes a hook-shaped cutting member 50. It is seen to comprise a shank portion 52 that terminates at its distal end in a downwardly curved hook portion 54 whose inside or concave surface is beveled or honed to provide a sharp cutting edge. The other end of the shank 52 is bent to form a rounded edge 58 leading to an elongated, terminal portion 60 which is affixed to a control rod 62 that extends through the lumen of the tubular barrel 12 and is connected to the slide lever 20 of the handle 16. In a similar fashion, electrical conductors, as at 64 and 66, extend through the handle 16 and through the tubular barrel 12 with the end of a first wire extending through one of the bores 28 or 30 to connect to one leg 38 or 40 of the electrode 36. The other conductor is fitted into one of the bores 32 or 34 and is connected to a leg of the second electrode 44. Conductors 64 and 66 are adapted to be connected to the terminals of an electrosurgical generator and the switch 18 is provided to control RF current flow to the electrodes 36 and 44.

The slot 46 extends through the wall of the electrode support member 26 as reflected by the unshaded surface 68 in the cross-sectioned distal end portion of the instrument as shown in FIG. 1. As is explained, this provides clearance for the cutting member to deflect during use.

In use for cutting and coagulating a tubular tissue structure, such as a branch vein leading off from the great saphenous vein in the leg of a patient, the instrument 10 will be inserted through a transversely extending incision in the leg of a patient and advanced until a branch vessel, as at 70, is made to enter the gap between the electrodes 36 and 44. The electrodes, being resilient wires, can deflect apart to assist entry of the vessel 70 therebetween. The slightly rounded and upturned and down turned ends of the electrodes assist in "funneling" the tissue structure into this gap. At this time, the cutting member 50, and especially its hook portion 54, is totally out of the gap between the electrodes and does not block entry of the tubular vessel therein.

Upon energization of the electrosurgical generator by actuation of the push-button switch 18 on the handle 16 of the instrument, a RF voltage sufficient to effect coagulation and sealing of the tubular tissue structure 70 in the area spanned by the legs of the U-shaped electrodes 36 and 44 is applied. Next, the surgeon can slide the lever 20 in the proximal direction in the slot 21 formed in the handle to draw back on the rod 62. This will cause the rounded edge segment 58 of the hook-shaped cutting member 50 to engage and slide down the ramp surface 48 in the slot 46 formed in the electrode support member 26 and causing the hook portion 54 to deflect down through the space between the legs 38 and 40 of the electrode 36 and enter the gap in which the tubular tissue structure 70 is contained. As the slide 20 is moved further rearward, the sharp cutting edge 56 of the hook-shaped cutting member 50 will pass through and sever the now coagulated tubular tissue structure.

In a similar fashion, the instrument of the present invention can be advanced to the next branch vein and the procedure repeated until all of the branch veins have been coagulated and severed. The harvested segment of the great saphenous vein may then be extracted through the transversely extending incision made in the leg of the patient and this is followed by the suturing of the several transverse incisions to close them.

ALTERNATIVE EMBODIMENT

Figure 4:
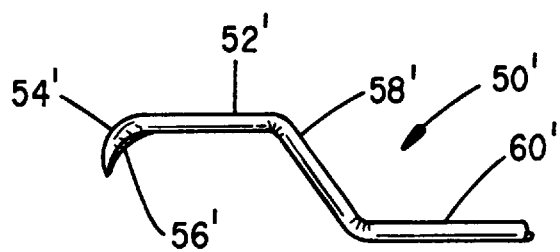
FIG. 4 is an enlarged partial view of an alternative of the instrument's cutting member.
Figure 5:
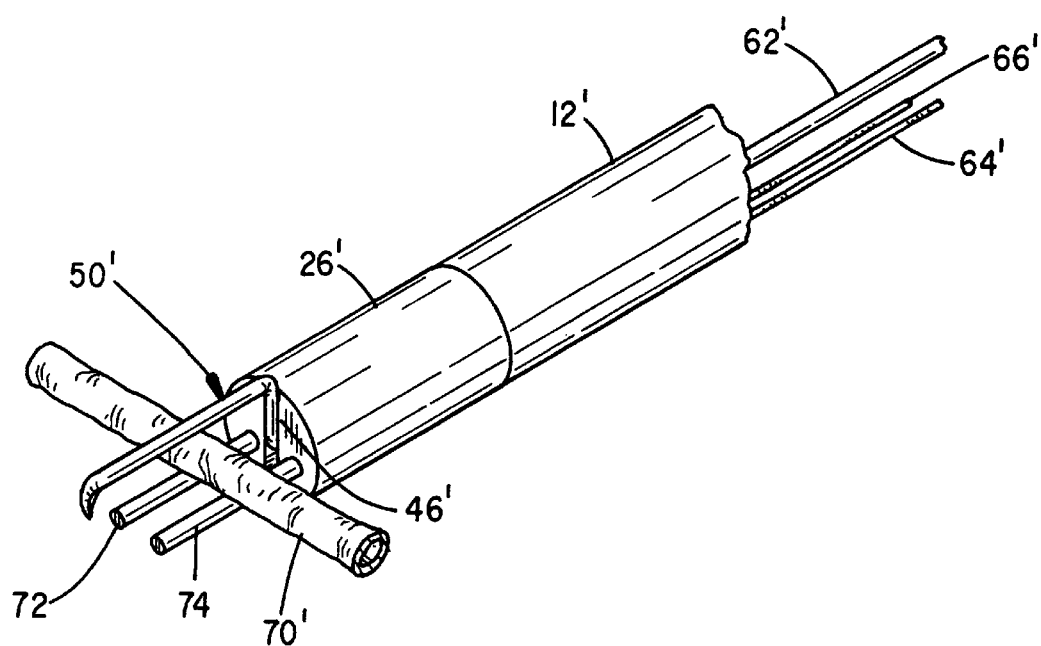
FIG. 5 is a partial perspective view of an alternative embodiment of the present invention.

Referring to FIGS. 4 and 5, there is shown the distal end portion of an alternative embodiment of the present invention. It differs from the earlier embodiment in the manner in which the coagulating electrodes are configured and in the shape of the cutting member 50. Instead of incorporating a pair of U-shaped electrodes disposed in parallel planes, one above the other, as shown in FIG. 1, in the embodiment of FIG. 5, the electrodes comprise first and second rectilinear conductive wire segments 72 and 74 which are inserted into longitudinal bores of the electrode support member 26'. The wires or rods comprising the electrodes 72, 74 are of generally equal length and are disposed in parallel, spaced-apart relationship to define a plane therebetween. The electrodes 72 and 74 are connected by electrical conductors 64' and 66' which lead through the lumen of the tubular barrel 12' and handle member (not shown) in the very same way as in the earlier described embodiment of FIG. 1.

Instead of locating the ramp in the slot 46' of the electrode support member 26', the hook shape cutting member 50' includes an incline portion 581 leading from shank 52' to control rod 60', all as can be seen in the enlarged partial view of FIG. 4. The control rod 62, again leads to a control lever on a handle in the same fashion as in the embodiment of FIG. 1.

In use, the instrument is advanced against a tubular tissue structure 70' to be coagulated for sealing and then cut. It is captured between the hook-shaped cutting member 50' and the electrode pair 72, 74 and when an RF voltage is applied across the electrodes, a coagulating current flows through the tissue. Now, by actuating the thumb slide 20 on the handle of the instrument, the ramp 58 of the hook-shaped cutting instrument 50' will engage the distal end of the electrode support member 26' above the slot until the cutting edge 56 intersects the plane of the electrodes 72 and 74. Further movement of the actuator 20 in the proximal direction will cause the cutting edge 56 to sever the tubular tissue structure 70'.

While the present invention has been described particularly for use in coagulating and then cutting venous branches when harvesting a vein segment for use in coronary bypass surgery, those skilled in the surgical arts will appreciate that the instrument may be used for other purposes, such as laparoscopic tubaligation or in vasectomy procedures and other instances where a tubular tissue segment is to be electrocoagulated and then cut.

ALTERNATIVE EMBODIMENT

Figure 6:
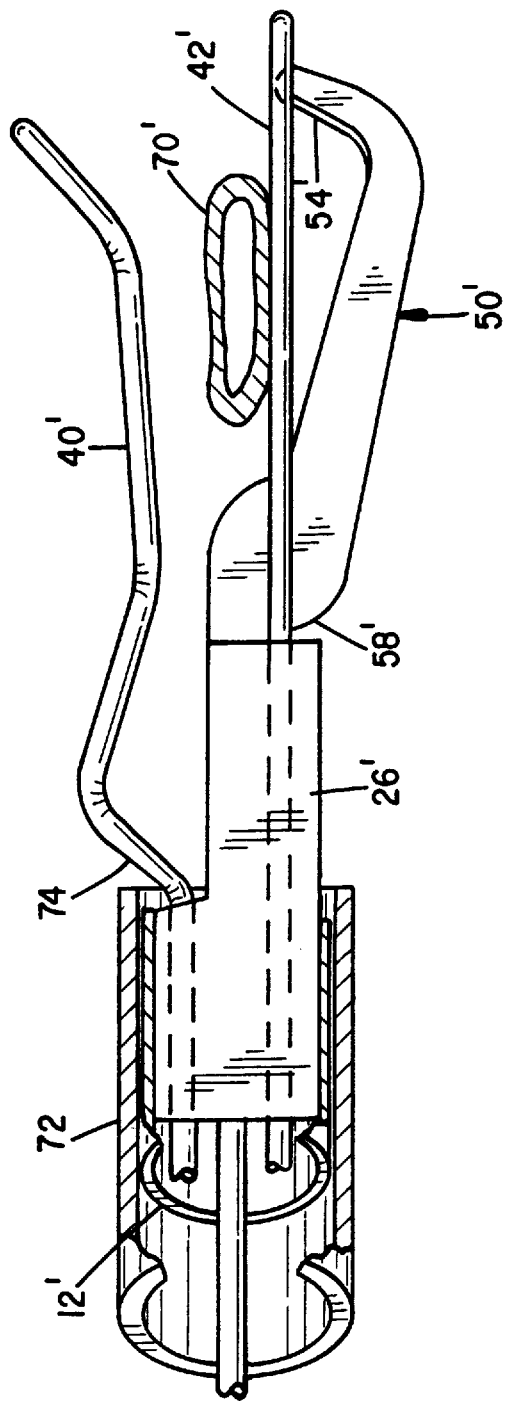
FIG. 6 is a partial cross-sectional view of the distal end portion of an alternative embodiment of the electrosurgical instrument of the present invention with the jaws thereof open.
Figure 7:
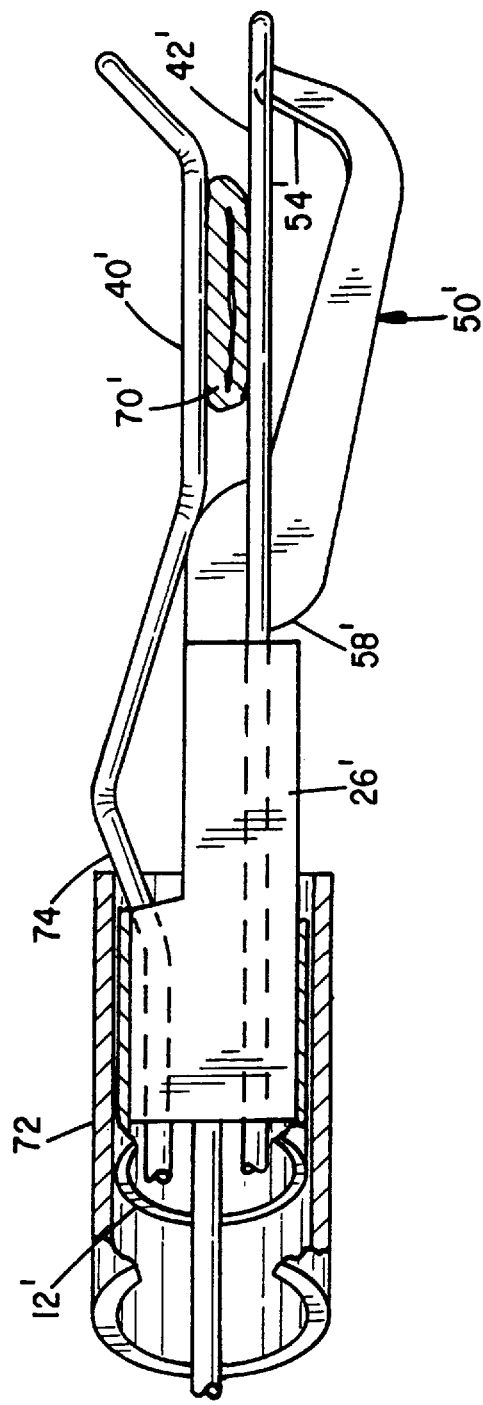
FIG. 7 is a partial cross-sectional view of the distal end portion of the alternative embodiment of the electrosurgical instrument with the jaws closed.
Figure 8:
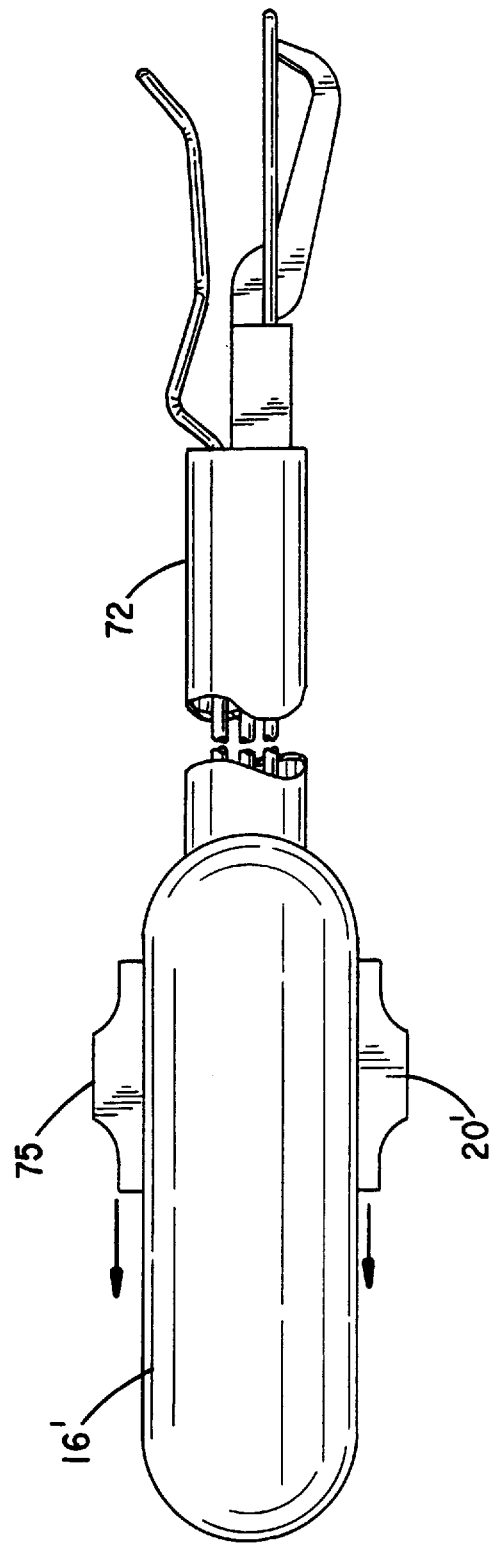
FIG. 8 is a side elevational view of the alternative embodiment.

FIGS. 6 through 8 illustrate an alternative embodiment of the electrosurgical instrument of the present invention. Rather than relying upon the resiliency of the wire electrodes to provide the requisite clamping force on the tissue structure as it is being cut, in the alternative embodiment, a positive clamping force is applied. In this arrangement, the tubular barrel 12' is coaxially surrounded by a longitudinally slideable sheath 72 that is operatively coupled to a thumb lever 74 disposed on the handle 16' so that reciprocal movement of the thumb lever 74 will slide the outer sheath 72 back and forth along the tubular barrel 12'. Fitted into the distal end of the barrel 12' is an insulating electrode support member 26' having longitudinally extending bores for receiving end portions of the U-shaped electrodes 40' and 42'. The electrode 40' is seen to include a ramp portion 74 integrally formed therewith where the ramp portion is closely adjacent to the distal end of the tubular member 12'.

As is shown in FIG. 7, as the outer sheath 72 is advanced in the distal direction by manipulation of the thumb slide 74 on the handle 16', the distal end of the sheath 72 comes into contact with and rides up the ramp 74, deflecting the electrode 40' toward the stationary electrode 421 and positively clamping the tissue structure 70' therebetween. Now, when the thumb switch 20' on the handle 16' is moved in the proximal direction, the blade 50' again will have its ramp portion 58' engage the end of the electrode support member 26' resulting in the cutting blade 50' deflecting upward through the loop defined by the U-shaped electrodes 42' and 40', with continued proximal displacement of the thumb lever 20' drawing the sharpened edge 54' of the blade through the tissue specimen 70'.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself. As an example, it is possible to affix one of the electrodes of the pair directly to the tubular barrel rather than to the electrode support member at the distal end of the barrel. Then, if the barrel is made of metal rather than of plastic, it can be covered by an insulating material to protect the user from shock and with the conductor means used to connect a power supply to the electrodes being attached one to the metal barrel and the other to the electrode that is supported in the support member.

What is claimed is:

1. An electrosurgical instrument for cutting and coagulating selected tissue structures comprising:

(a) an elongated tubular barrel having a proximal end, a distal end and a lumen extending therebetween;

(b) a handle attached to the proximal end of the barrel;

(c) a pair of resilient, metal wire electrodes, each having a pair of legs joined at one end thereof to form a generally U-shape;

(d) an electrode support member affixed to the distal end of the barrel for supporting at least one of the pair of electrodes in parallel, spaced-apart, cantilevered relation to the other of the pair of electrodes at the distal end of the barrel with a predetermined gap therebetween, the support member including at least one pair of bores, at least one of the at least one pair of bores communicating with the lumen of the barrel for receiving the legs of the at least one pair of electrodes therein, and a longitudinal slot extending transverse to planes in which the legs of the pair of electrodes reside midway between the pairs of legs of the electrodes;

(e) a cutting member disposed in the slot and longitudinally movable therein, one of the cutting member and the slot including an inclined segment;

(f) actuator means disposed on the handle and coupled to the cutting member for imparting reciprocal longitudinal translation of the cutting member where the longitudinal translation engages the inclined segment on the one of the cutting member and the slot with an edge surface of the other of the cutting member and the slot to deflect the cutting member between the legs of the electrodes; and (g) conductor means extending through the handle, the lumen of the barrel and the at least one of the at least one pair of bores and adapted to connect the pair of electrodes to a voltage source.

2. The electrosurgical instrument as in claim 1 wherein the predetermined gap is adapted to be less than the thickness of the selected tissue structures to be cut and coagulated with the pair of electrodes gripping the selected tissue structures when inserted between the pair of electrodes.

3. The electrosurgical instrument as in claim 1 wherein the cutting member is hook-shaped.

4. The electrosurgical instrument as in claim 3 wherein the hook-shaped cutting member is movable from a first position where the hook-shaped cutting member resides out of the gap to a second position in the gap and abutting the electrode support member upon actuation of the actuator means.

5. The electrosurgical instrument as in claim 3 wherein a concave portion of the hook-shaped cutting member is beveled to create a cutting edge.

6. The electrosurgical instrument as in claim 1 wherein the conductor means includes a control switch.

7. The electrosurgical instrument as in claim 3 wherein the actuator means comprises a finger operable member and a generally rigid rod coupling the finger operable member to the hook-shaped cutting member.

8. The electrosurgical instrument as in claim 7 wherein the hook-shaped cutting member comprises a shank portion terminating at a distal end in a hook portion and at a proximal end in the inclined segment, the generally rigid rod being connected to an end of the inclined segment, the hook portion including a sharpened cutting edge.

9. The electrosurgical instrument as in claim 2 wherein movement of the actuator means in a proximal direction engages an edge on the cutting member with a ramp surface in the slot for forcing the cutting member into the gap between the pair of electrodes and against the tissue structures being gripped therebetween.

10. The electrosurgical instrument as in claim 2 wherein movement of the actuator means in a proximal direction engages an inclined segment on the cutting member with an edge of the slot for forcing the cutting member into the gap between the pair of electrodes and against the tissue structure being gripped therebetween.

11. An electrosurgical instrument for cutting and coagulating tubular tissue structures comprising:
   (a) an elongated tubular barrel having a proximal end, a distal end and a lumen extending therebetween;
   (b) a handle attached to the proximal end of the barrel;
   (c) a pair of metal wire electrodes;
   (d) an electrode support member affixed to the distal end of the barrel for supporting at least one of the pair of electrodes in parallel, spaced-apart, cantilevered relation at the distal end of the barrel, the support member including at least one bore communicating with the lumen of the barrel for receiving the at least one pair of electrodes therein, and a longitudinal slot extending transverse to a plane in which the pair of electrodes reside midway between the electrodes;
   (e) a hook-shaped cutting member disposed in the slot and longitudinally movable therein, one of the hook-shaped cutting member and the slot including an inclined segment;
   (f) actuator means disposed on the handle and coupled to the hook-shaped cutting member for imparting reciprocal longitudinal translation and transverse movement of the hook-shaped cutting member where the longitudinal translation engages the inclined segment on the one of the cutting member and the slot with an edge surface of the other of the cutting member and the slot to deflect the cutting member between the pair of electrodes; and
   (g) conductor means extending through the handle, the lumen of the barrel and the at least one bore, the conductor means adapted to connect the electrodes to a voltage source.

12. The electrosurgical instrument as in claim 11 wherein the hook-shaped cutting member comprises a shank portion terminating at a distal end in a hook portion and at a proximal end in the inclined segment, a generally rigid rod being connected to an end of the inclined segment, the hook portion including a sharpened cutting edge.

13. The electrosurgical instrument as in claim 12 wherein the metal wire electrodes are rectilinear.

14. The electrosurgical instrument as in claim 13 wherein the hook-shaped cutting member is movable from a first position where the hook-shaped cutting member overlays the plane by a predetermined gap distance to a second position where the hook-shaped cutting member intersects the plane upon actuation of the actuator means.

15. The electrosurgical instrument as in claim 14 wherein a concave portion of the hook-shaped cutting member is beveled to create a cutting edge.

16. The electrosurgical instrument as in claim 13 wherein movement of the actuator means in a proximal direction engages an inclined segment of the hook-shaped cutting member with an edge of the slot for forcing the cutting member into a space between the pair of electrodes and against a tubular tissue structure disposed between the pair of electrodes and the hook-shaped cutting member.

17. The electrosurgical instrument as in claim 13 wherein movement of the actuator means in a proximal direction engages an edge on the hook-shaped cutting member with an inclined segment of the slot for forcing the cutting member into a space between the pair of electrodes and against a tubular tissue structure disposed between the pair of electrodes and the hook-shaped cutting member.

18. The electrosurgical instrument as in claim 11 and further including an outer sheath concentrically disposed on and slidable along the tubular barrel, the sheath having a proximal end and a distal end and wherein one of the pair of electrodes includes a ramp surface thereon whereby sliding the distal end of the sheath against the ramp surface on the one of the pair of electrodes displaces the one of the pair of electrodes toward the other of the pair of electrodes.

19. The electrosurgical instrument as in claim 18 and further including actuator means on the handle operatively coupled to said sheath for imparting reciprocal motion thereto.

* * * * *